(12) United States Patent
Cui et al.

(10) Patent No.: US 8,110,654 B2
(45) Date of Patent: Feb. 7, 2012

(54) T CELL EPITOPE PEPTIDES OF OVARIAN CANCER ANTI-IDIOTYPIC ANTIBODY 6B11 AND USE THEREOF

(75) Inventors: Heng Cui, Beijing (CN); Wei Li, Beijing (CN); Xiaohong Chang, Beijing (CN); Jie Feng, Beijing (CN); Hongyan Cheng, Beijing (CN); Huifang Guo, Beijing (CN); Yexia Cheng, Beijing (CN)

(73) Assignee: Peking University People;s Hospital, Beijing (CN)

( * ) Notice: Subject to any disclaimer, the term of this patent is extended or adjusted under 35 U.S.C. 154(b) by 138 days.

(21) Appl. No.: 12/303,244

(22) PCT Filed: Jun. 4, 2007

(86) PCT No.: PCT/CN2007/001769
§ 371 (c)(1),
(2), (4) Date: Jul. 6, 2009

(87) PCT Pub. No.: WO2007/143917
PCT Pub. Date: Dec. 21, 2007

(65) Prior Publication Data
US 2009/0269366 A1    Oct. 29, 2009

(30) Foreign Application Priority Data
Jun. 2, 2006 (CN) .......................... 2006 1 0083299

(51) Int. Cl.
| | |
|---|---|
| A61K 38/00 | (2006.01) |
| C07K 2/00 | (2006.01) |
| C07K 4/00 | (2006.01) |
| C07K 5/00 | (2006.01) |
| C07K 7/00 | (2006.01) |
| C07K 14/00 | (2006.01) |
| C07K 16/00 | (2006.01) |
| C07K 17/00 | (2006.01) |
| A61K 38/04 | (2006.01) |
| A61K 38/10 | (2006.01) |
| A61K 38/08 | (2006.01) |
| A61P 35/00 | (2006.01) |

(52) U.S. Cl. ....... 530/300; 530/327; 530/328; 514/19.2; 514/19.3; 514/21.5; 514/21.6

(58) Field of Classification Search .......................... None
See application file for complete search history.

(56) References Cited

U.S. PATENT DOCUMENTS
5,502,167 A * 3/1996 Waldmann et al. ......... 530/387.3
2008/0199851 A1* 8/2008 Egan et al. ......................... 435/5

FOREIGN PATENT DOCUMENTS
| CN | 1356341 A | 7/2002 |
|---|---|---|
| CN | 1528452 A | 9/2004 |
| CN | 1679930 A | 10/2005 |
| CN | 1718243 A | 1/2006 |
| CN | 1727362 A | 2/2006 |

OTHER PUBLICATIONS

Wheeler. Preventive vaccines for cervical cancer. Salud publica de Mexico, 1997. vol. 39. pp. 1-9.*
Efferson, Kawano, Tsuda, Palese, Garcia-Sastre, and Ioannides. Stimulation of human T cells by an influenza A vector expressing a CTL epitope from the HER-2/neu protooncogene results in higher numbers of antigen-specific TCRhi cells than stimulation with peptide. Anticancer Research, 2005. vol. 25, pp. 715-724.*
Bachman, Wolint, Schwarz, and Oxenius. Recall proliferation potential of memory CD8+ T cells and antiviral protection. Journal of Immunology, 2005. vol. 175, pp. 4677-4685.*
Granziero, Krajewski, Farness, Yuan, Courtney, Jackson, Peterson, and Vitiello. Adoptive immunotherapy prevents prostate cancer in a transgenic animal model. European Journal of Immunology, 1999. vol. 29, pp. 1127-1138.*
Byers. What can randomized controlled trials tell us about nutrition and cancer prevention? CA Cancer Journal for Clinicians, 1999. vol. 49, pp. 353-361.*
Chang, Xiaohong et al, Specific humoral immune response induced by peptides of 6B11 ovarian cancer anti-idiotypic antibody, Chin J Clin Obstet Gynecol May 2005, vol. 6, No. 3, pp. 204-207.
Chinese Patent Office; International Search Report for PCT/CN2007/001769, mailed Sep. 20, 2007.
Li, Wei et al, New T cell epitopes identified from an anti-idiotypic antibody mimicking ovarian cancer associated antigen, Cancer Immunol Immunother (2008) 57:143-154 (Article published Jul. 6, 2007).

* cited by examiner

Primary Examiner — Anne M. Gussow
(74) Attorney, Agent, or Firm — Perkins Coie LLP; Yingli Wang

(57) ABSTRACT

The present invention provides two T-cell epitope peptides of anti-idiotype antibody 6B11 of ovarian cancer, the sequences of which are shown in SEQ ID NO:3 or 6. The present invention also provides the use of such T-cell epitope peptides in the manufacture of vaccines against ovarian cancer and in the treatment and prevention of ovarian cancer. The T-cell epitope peptides of the present invention could specifically kill ovarian cancer cells which are OC166-9 positive, and could find a wide use in the treatment and prevention of ovarian cancer.

9 Claims, 11 Drawing Sheets

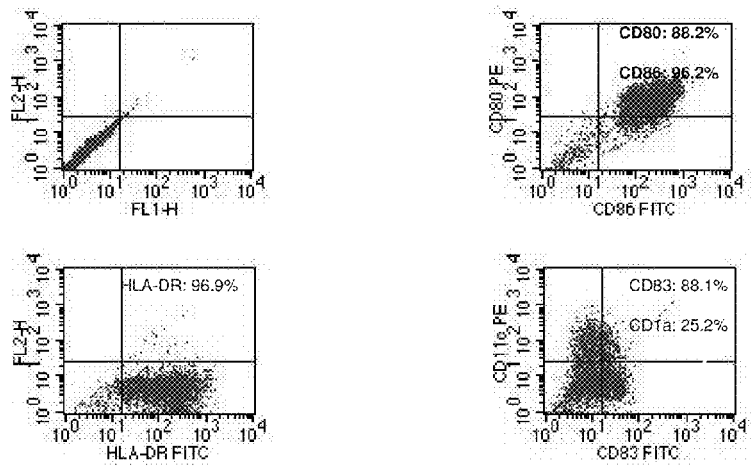
Fig. 1 expression profile of the surface molecules of mature dendritic cells
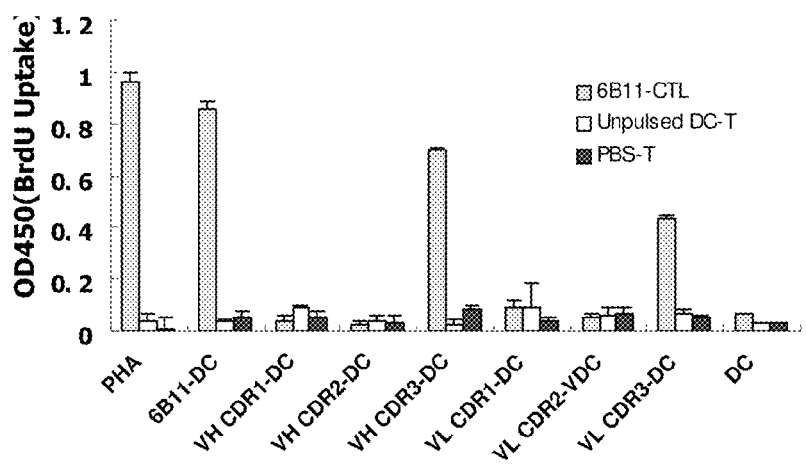
Fig. 2 BrdU cell proliferation assay

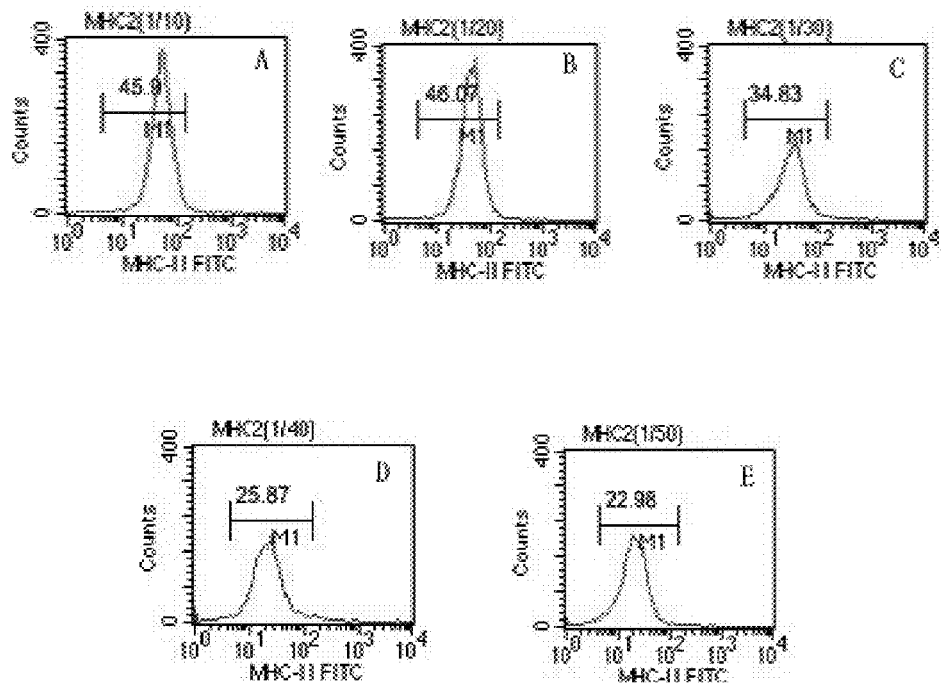
Fig. 3 determination of the optimal application concentration of MHC class II molecule antibodies
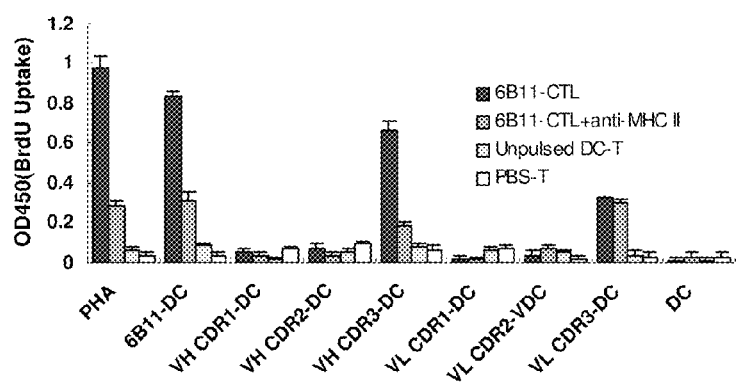
Fig. 4 BrdU cell proliferation assay after applying MHC class II molecule blocking antibodies

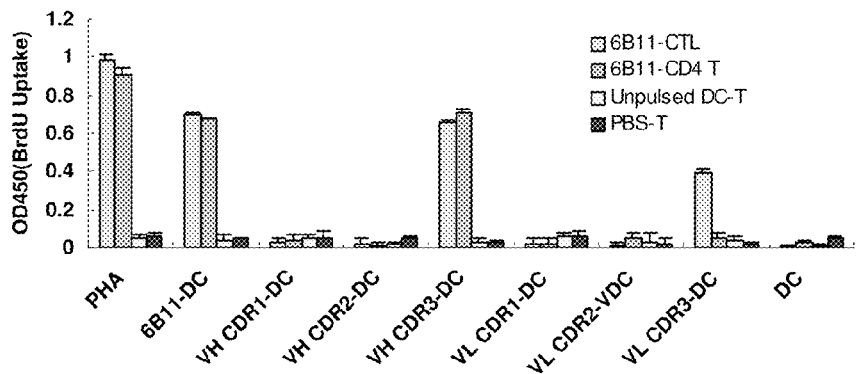
Fig. 5  BrdU cell proliferation assay after sorting CD4 T cells
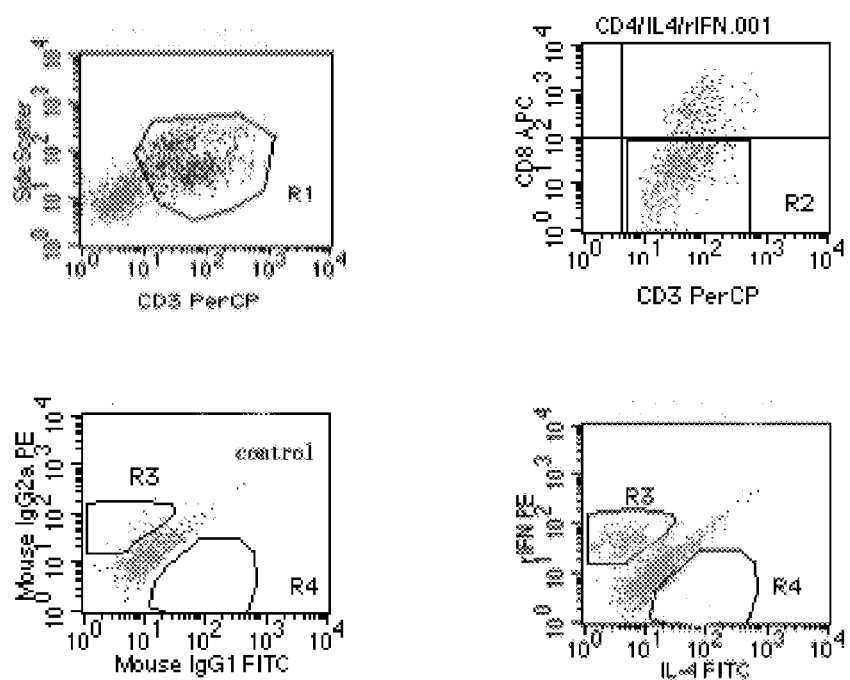
Fig. 6  determination of the intracellular cytokines of CD4 T cells by flow cytometry

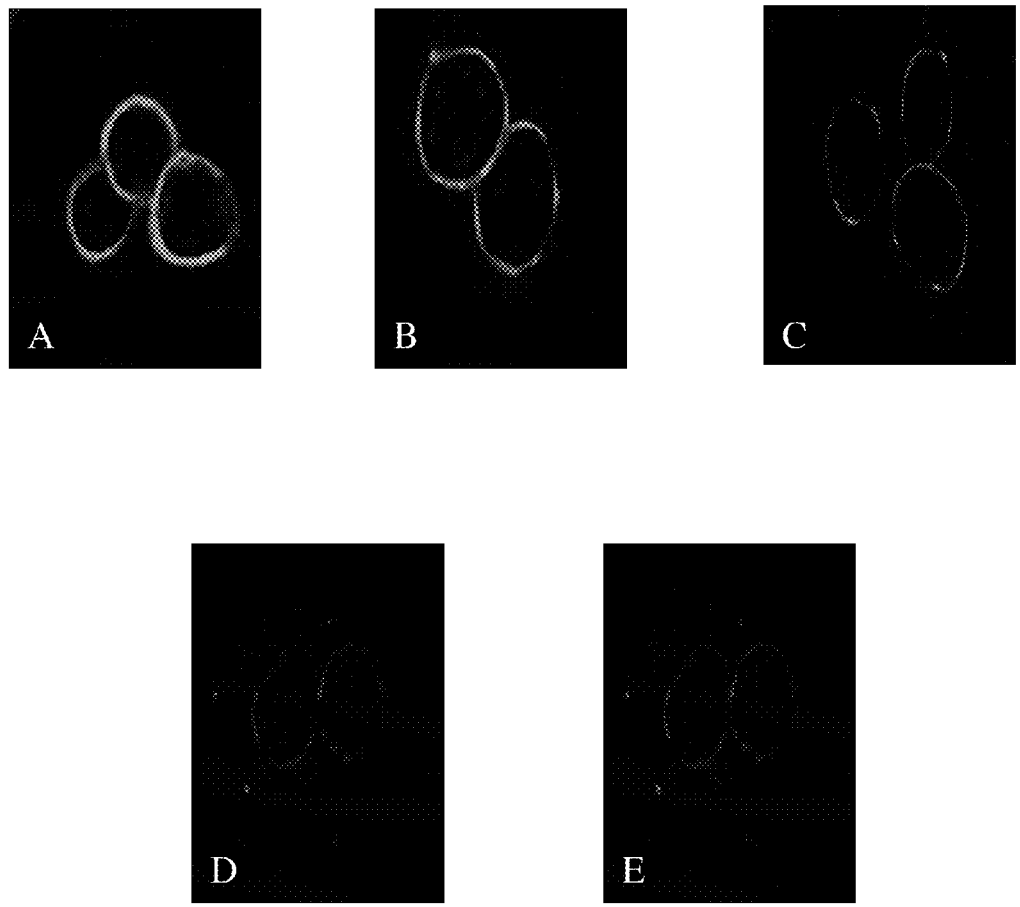
A: high affinity peptide, B: moderate affinity peptide, C: low affinity peptide, D: no affinity peptide, E: T2 cells alone
Fig. 7 detection of the expression profile of MHC-I molecules on the surface of T2 cells (co-incubated with 30 μg/ml peptides) by confocal microscopy

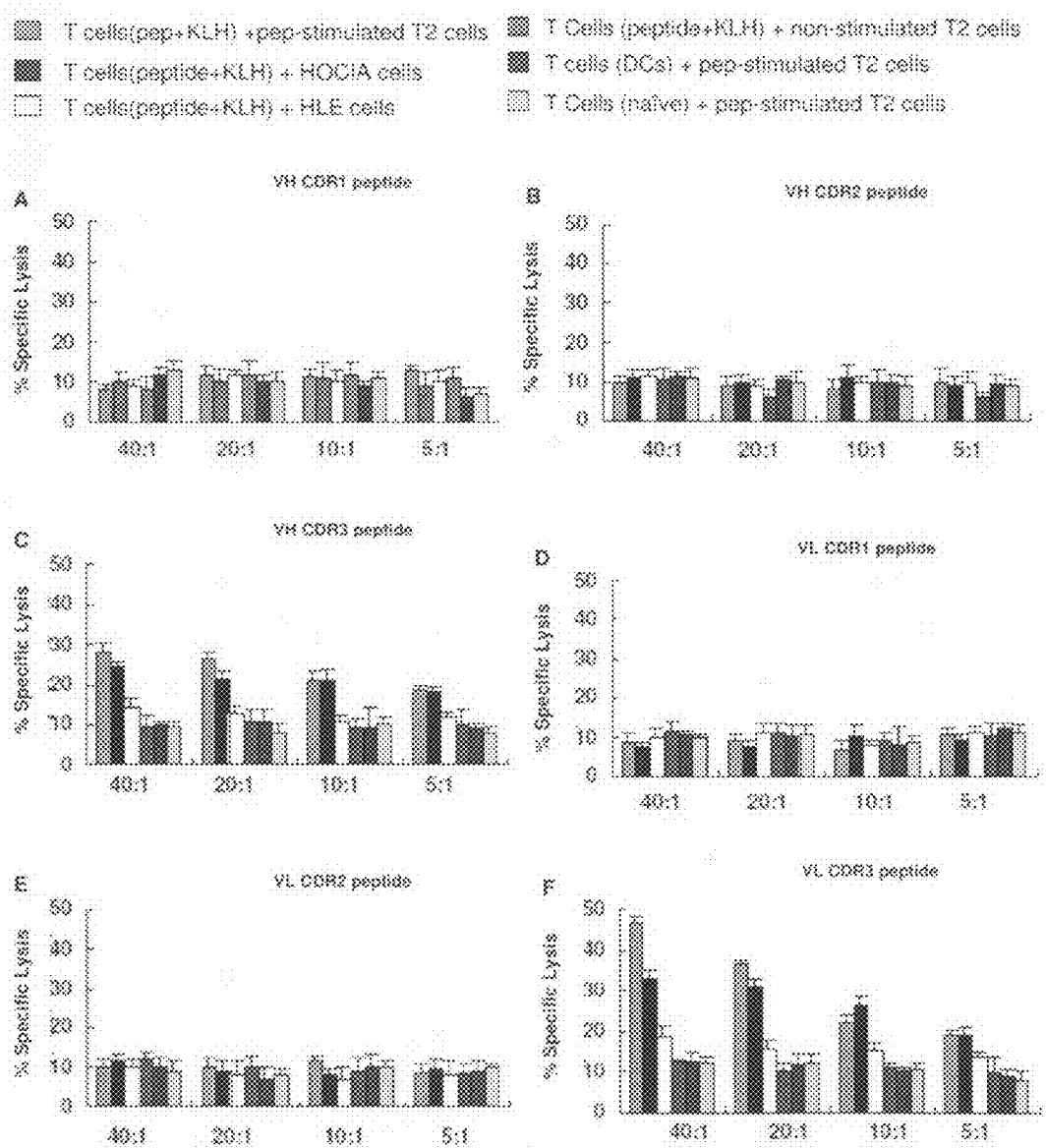

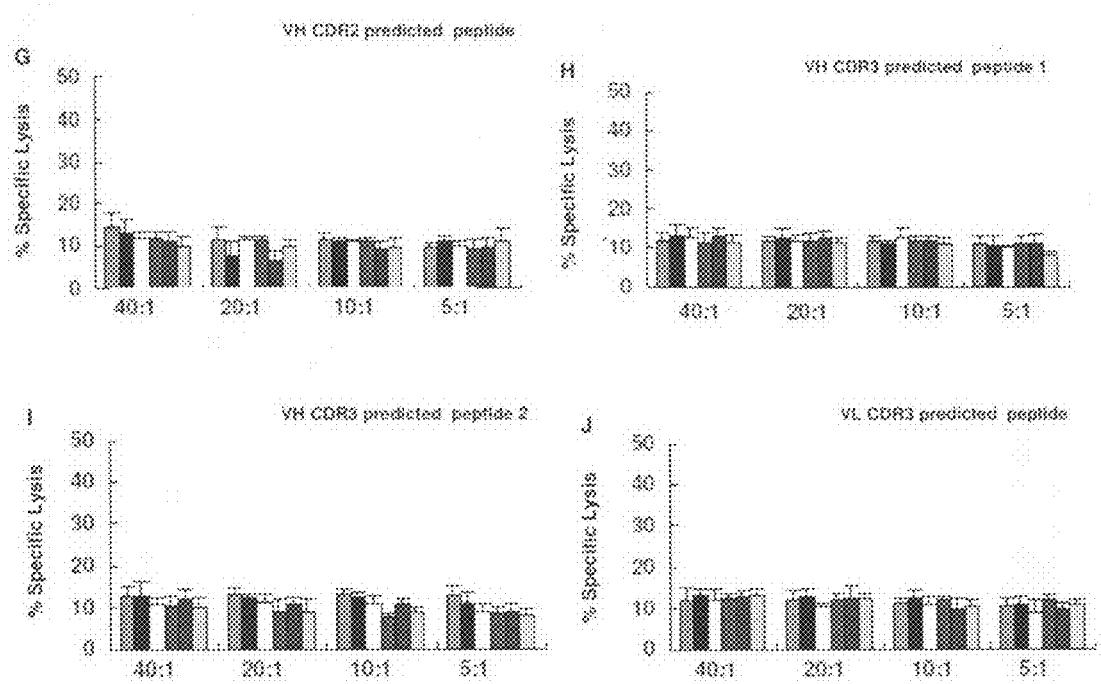

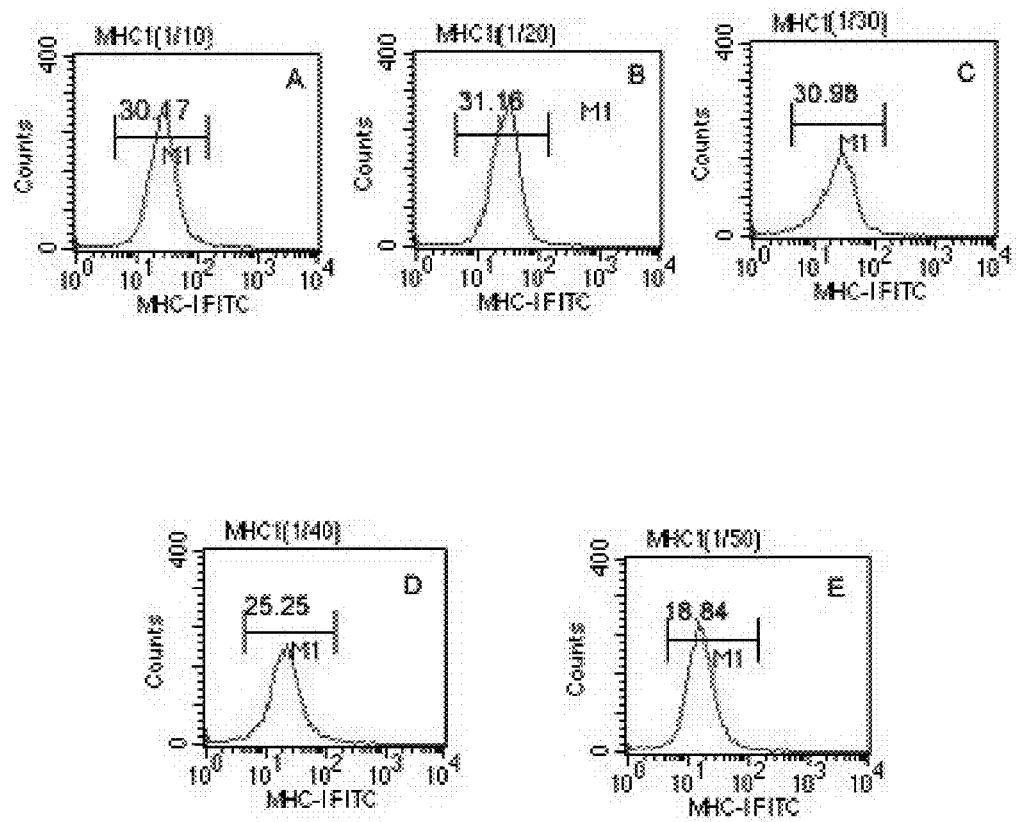
Fig. 9 determination of the optimal application concentration of MHC class I molecule antibodies

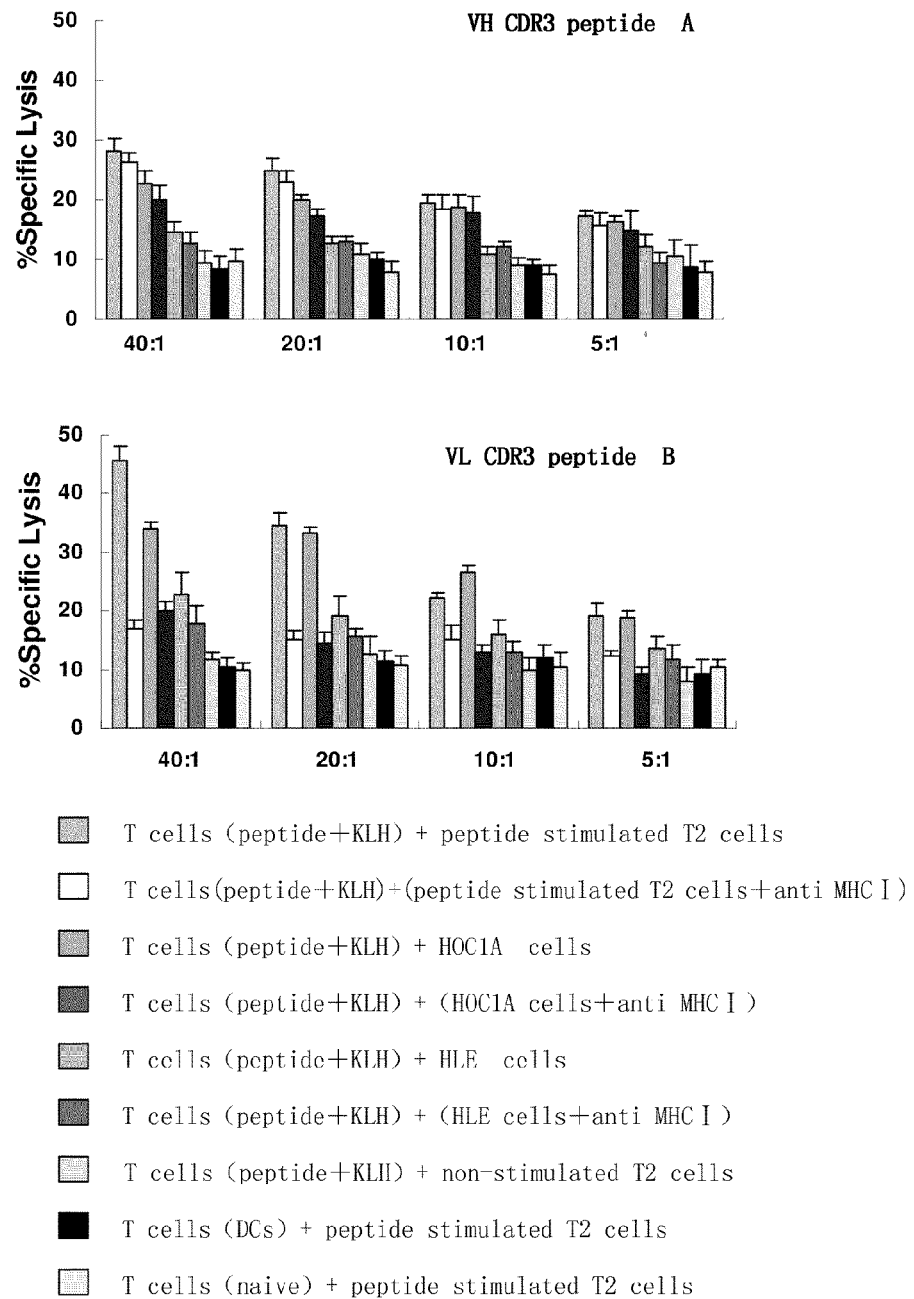
Fig. 10 $^{51}$Cr release assay on the VH CDR3 and VL CDR3 peptide specific CTLs after MHC class I molecule antibody blocking

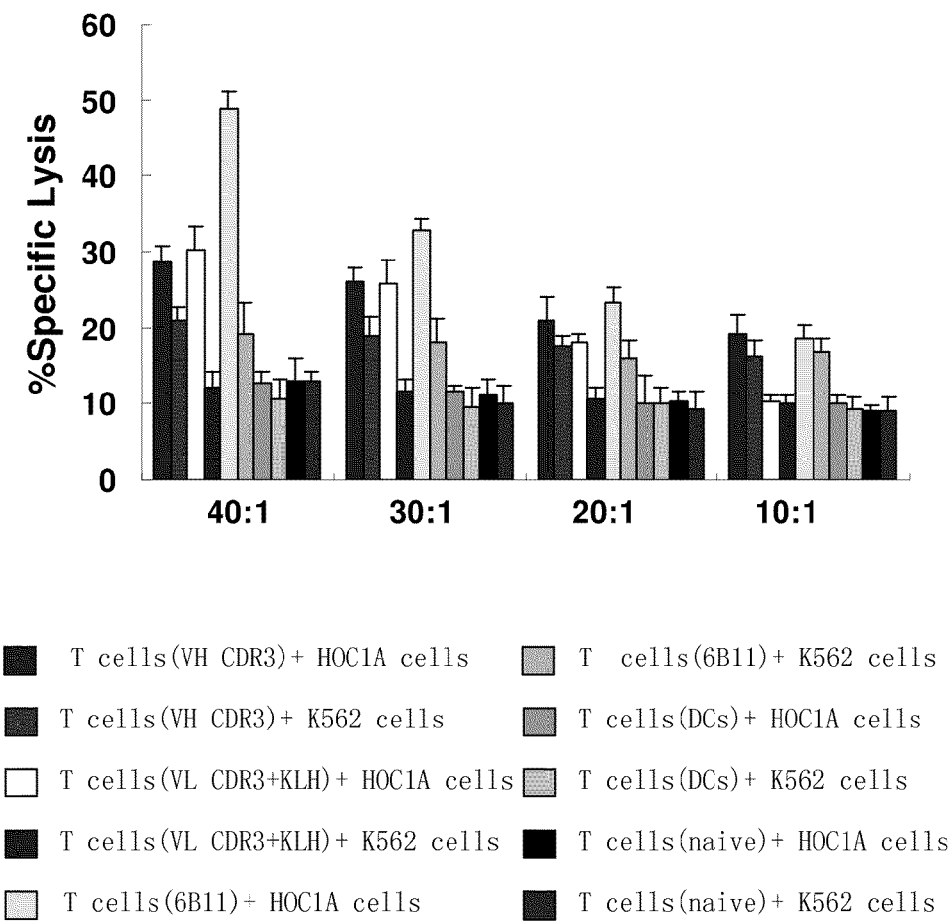
Fig. 11 detection of killing effects of the VH CDR3 and VL CDR3 peptide specific CTLs on K562 cells by $^{51}$Cr release assay

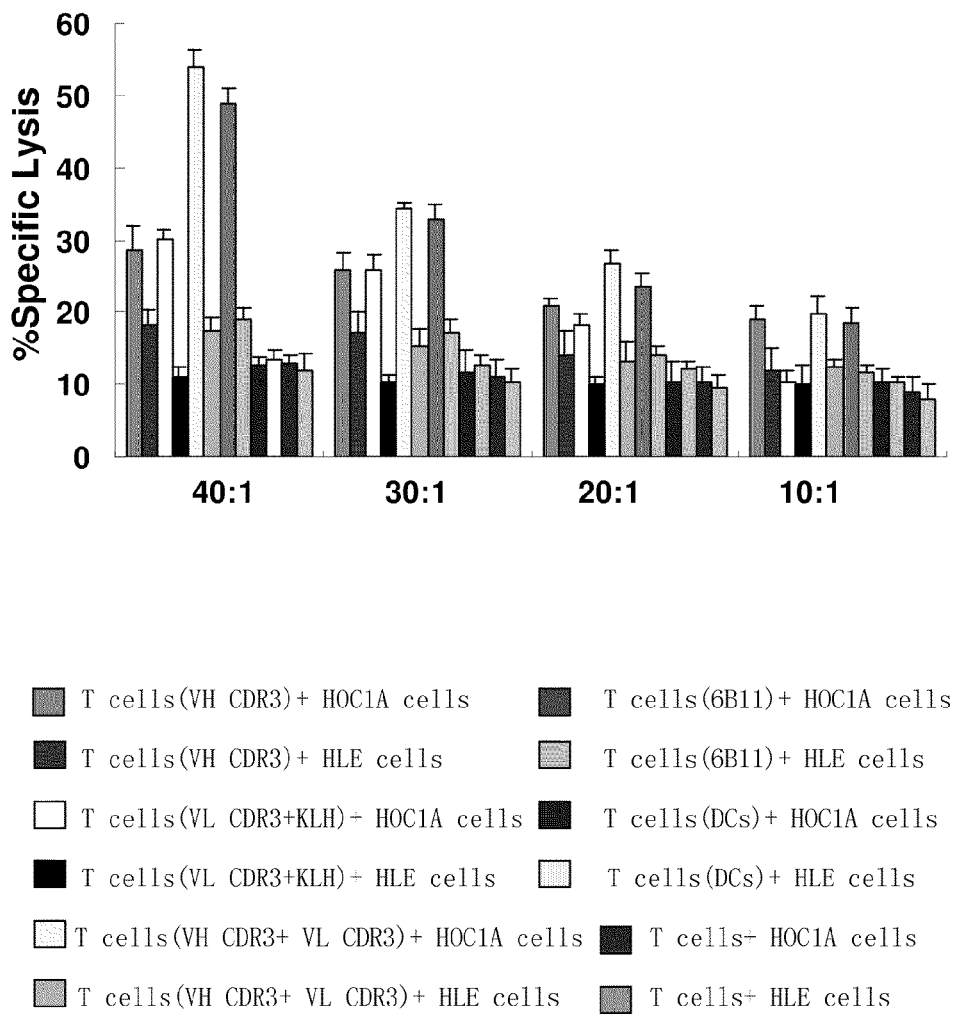
Fig. 12 detection of effectiveness of killing ovarian cancer cells by the VH CDR3 and VL CDR3 peptide specific CTLs through $^{51}$Cr release assay

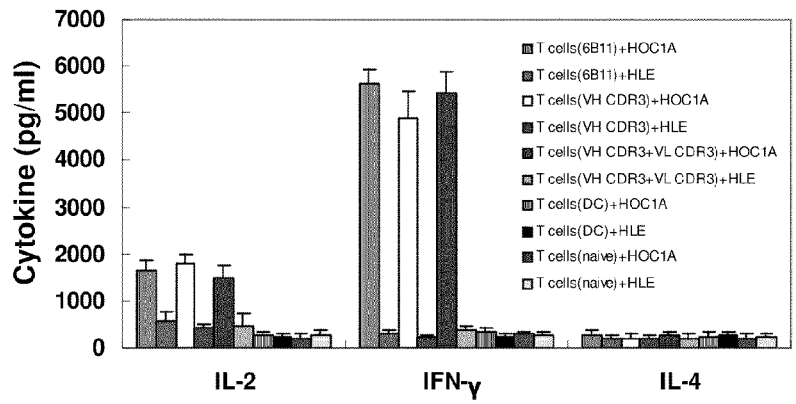
Fig. 13 expression profiles of cytokines of CTLs induced by VH CDR3 and VL CDR3 peptides as well as anti-idiotype antibody 6B11
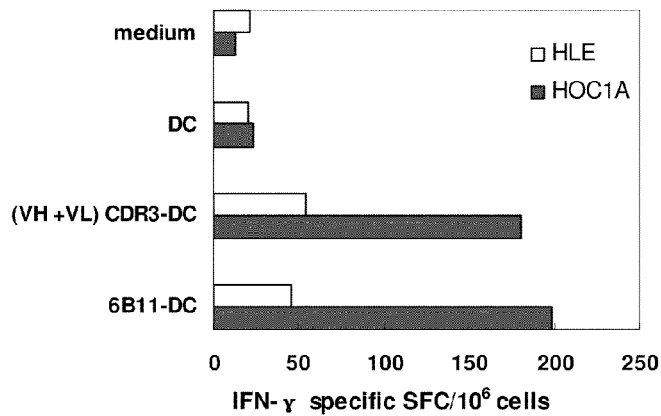
Fig. 14 profiles of antigen-specifc IFN-γ-producing cells among anti-idiotype antibody 6B11-CTLs as well as VH CDR3 and VL CDR3 region peptides specific CTLs

```
                        SEQUENCE LISTING

<160> NUMBER OF SEQ ID NOS: 18

<210> SEQ ID NO 1
<211> LENGTH: 8
<212> TYPE: PRT
<213> ORGANISM: artificial sequence
<220> FEATURE:
<223> OTHER INFORMATION: VH CDR1 region peptide

<400> SEQUENCE: 1

Pro Thr Tyr Gly Ile Gly Val Gly
1               5

<210> SEQ ID NO 2
<211> LENGTH: 16
<212> TYPE: PRT
<213> ORGANISM: artificial sequence
<220> FEATURE:
<223> OTHER INFORMATION: VH CDR2 region peptide

<400> SEQUENCE: 2

His Ile Trp Trp Asn Asn Asn Lys Tyr Tyr Asn Thr Ala Leu Lys Ser
1               5                   10                  15

<210> SEQ ID NO 3
<211> LENGTH: 14
<212> TYPE: PRT
<213> ORGANISM: artificial sequence
<220> FEATURE:
<223> OTHER INFORMATION: VH CDR3 region peptide

<400> SEQUENCE: 3

Ile Ala Leu Ile Thr Thr Lys Ile Ala Trp Tyr Phe Asp Val
1               5                   10

<210> SEQ ID NO 4
<211> LENGTH: 16
<212> TYPE: PRT
<213> ORGANISM: artificial sequence
<220> FEATURE:
<223> OTHER INFORMATION: VL CDR1 region peptide

<400> SEQUENCE: 4

Arg Ser Ser Gln Asn Leu Val His Ser Asn Gly Asn Thr Tyr Leu His
1               5                   10                  15

<210> SEQ ID NO 5
<211> LENGTH: 8
<212> TYPE: PRT
<213> ORGANISM: artificial sequence
<220> FEATURE:
<223> OTHER INFORMATION: VL CDR2 region peptide
```

-continued

```
<400> SEQUENCE: 5

Pro Ile Val Ser Asn Arg Phe Ser
1               5

<210> SEQ ID NO 6
<211> LENGTH: 9
<212> TYPE: PRT
<213> ORGANISM: artificial sequence
<220> FEATURE:
<223> OTHER INFORMATION: VL CDR3 region peptide

<400> SEQUENCE: 6

Ser Gln Ser Thr His Phe Pro Tyr Thr
1               5

<210> SEQ ID NO 7
<211> LENGTH: 9
<212> TYPE: PRT
<213> ORGANISM: artificial sequence
<220> FEATURE:
<223> OTHER INFORMATION: predicted peptide

<400> SEQUENCE: 7

His Ile Trp Trp Asn Asn Asn Lys Tyr
1               5

<210> SEQ ID NO 8
<211> LENGTH: 9
<212> TYPE: PRT
<213> ORGANISM: artificial sequence
<220> FEATURE:
<223> OTHER INFORMATION: predicted peptide

<400> SEQUENCE: 8

Asn Asn Lys Tyr Tyr Asn Thr Ala Leu
1               5

<210> SEQ ID NO 9
<211> LENGTH: 9
<212> TYPE: PRT
<213> ORGANISM: artificial sequence
<220> FEATURE:
<223> OTHER INFORMATION: predicted peptide

<400> SEQUENCE: 9

Asn Asn Asn Lys Tyr Tyr Asn Thr Ala
1               5

<210> SEQ ID NO 10
<211> LENGTH: 9
<212> TYPE: PRT
<213> ORGANISM: artificial sequence
<220> FEATURE:
<223> OTHER INFORMATION: predicted peptide

<400> SEQUENCE: 10

Trp Asn Asn Asn Lys Tyr Tyr Asn Thr
1               5

<210> SEQ ID NO 11
<211> LENGTH: 9
<212> TYPE: PRT
<213> ORGANISM: artificial sequence
<220> FEATURE:
<223> OTHER INFORMATION: predicted peptide

<400> SEQUENCE: 11
```

```
Leu Ile Thr Thr Lys Ile Ala Trp Tyr
1               5

<210> SEQ ID NO 12
<211> LENGTH: 9
<212> TYPE: PRT
<213> ORGANISM: artificial sequence
<220> FEATURE:
<223> OTHER INFORMATION: predicted peptide

<400> SEQUENCE: 12

Ala Leu Ile Thr Thr Lys Ile Ala Trp
1               5

<210> SEQ ID NO 13
<211> LENGTH: 9
<212> TYPE: PRT
<213> ORGANISM: artificial sequence
<220> FEATURE:
<223> OTHER INFORMATION: predicted peptide

<400> SEQUENCE: 13

Ile Ala Leu Ile Thr Thr Lys Ile Ala
1               5

<210> SEQ ID NO 14
<211> LENGTH: 9
<212> TYPE: PRT
<213> ORGANISM: artificial sequence
<220> FEATURE:
<223> OTHER INFORMATION: predicted peptide

<400> SEQUENCE: 14

Thr Lys Ile Ala Trp Tyr Phe Asp Val
1               5

<210> SEQ ID NO 15
<211> LENGTH: 9
<212> TYPE: PRT
<213> ORGANISM: artificial sequence
<220> FEATURE:
<223> OTHER INFORMATION: predicted peptide

<400> SEQUENCE: 15

Asn Leu Val His Ser Asn Gly Asn Thr
1               5

<210> SEQ ID NO 16
<211> LENGTH: 9
<212> TYPE: PRT
<213> ORGANISM: artificial sequence
<220> FEATURE:
<223> OTHER INFORMATION: predicted peptide

<400> SEQUENCE: 16

Val His Ser Asn Gly Asn Thr Tyr Leu
1               5

<210> SEQ ID NO 17
<211> LENGTH: 9
<212> TYPE: PRT
<213> ORGANISM: artificial sequence
<220> FEATURE:
<223> OTHER INFORMATION: predicted peptide

<400> SEQUENCE: 17

Ser Ser Gln Asn Leu Val His Ser Asn
1               5
```

```
<210> SEQ ID NO 18
<211> LENGTH: 9
<212> TYPE: PRT
<213> ORGANISM: artificial sequence
<220> FEATURE:
<223> OTHER INFORMATION: predicted peptide

<400> SEQUENCE: 18

Leu Val His Ser Asn Gly Asn Thr Tyr
1               5
```

T CELL EPITOPE PEPTIDES OF OVARIAN CANCER ANTI-IDIOTYPIC ANTIBODY 6B11 AND USE THEREOF This application is a national stage application of International Application No. PCT/CN2007/001769, filed Jun. 4, 2007, which claims priority to Chinese Patent Application No. 200610083299.7, filed Jun. 2, 2006, both of which are incorporated herein by reference.

TECHNICAL FIELD

The present invention relates to two T-cell epitode peptides of ovarian cancer anti-idiotype antibody 6B11 and to the use of such peptides for increasing a cellular immune response against ovarian cancer.

BACKGROUND ART

Ovarian cancer severely affects women's health. Its morbidity ranks second among all the gynecologic malignant tumors while its morality ranks first. Ovarian cancer is a major cause for the death caused by gynecologic malignant tumors. Its onset is difficult to be noticed, while its progression is very fast. Among all the patients with ovarian cancer, 70-80% of them are diagnosed at a late stage. The 5-year survival rate of ovarian cancer patients is only about 30%. Neither the efficacy of traditional surgery nor that of chemical therapy is satisfactory. More than 70% of ovarian cancer will progress or relapse, even though the disease has been controlled temporarily. Further treatment will be even more difficult. Therefore, there is a need for a more effective therapy to increase the survival rate and improve the life quality of the patients with ovarian cancer.

Biological therapy is the fourth major tumor therapy while the other three are traditional surgery, radiation therapy and chemical therapy. As one type of biological therapies against tumors, tumor vaccine therapy has become a beneficial supplement to traditional therapies and has been used in the clinical treatment for many malignant tumors, because tumor vaccine can induce positive anti-tumor effect by the organism's immune system and it is both specific and targetable.

With continuous progress of biotechnology and more knowledge of the organisms' immune responses, tumor vaccine has been extensively developed. Tumor vaccine mainly comprises cell vaccine, antigen vaccine, anti-idiotype vaccine, peptide vaccine or epitope vaccine. Cell vaccine against a tumor is derived from auto- or allo-tumor cells or the rude extract thereof. Since it contains all the tumor antigens of an individual, it can induce an anti-tumor immune response to a certain extent. However, disadvantages such as oncogenicity and weak immunogenicity still exist. Antigen vaccine is a tumor specific or tumor associated antigen which is extracted from tumor cells. Its composition is more definite than cell vaccines, and the oncogenicity and auto immune response are reduced. Anti-idiotype vaccine is an internal image mimicking a key epitope of a tumor antigen, which is different from the original tumor antigen. Upon administration, it can destroy the immune tolerance which is inherent in organisms with tumors and trigger specific immune response by the organisms per se. Its preparation is easier than that of antigen vaccine and the side effect is slight. Peptide vaccine is a peptide with a pivotal anti-tumor effect. It is clear now that any tumor antigen shall firstly be degraded into short peptides by antigen presenting cells; then the key epitope peptides therein bind to major histocompatibility complex (MHC) molecules, thus triggering the anti-tumor effects of immune cells. It can be seen that the development of tumor vaccine is a progressive scientific exploration and epitope peptides bring out a new route for developing tumor vaccines in the future.

Epitope is a special chemical group within an antigen molecule which determines the antigenic specificity of an antigen, also known as antigenic determinant. Epitope is a basic unit for specific binding with T- or B-cell receptors and antibodies. In an immune response, the antigen epitopes recognized by T cells and B cells are different, which are called as T cell epitopes and B cell epitopes respectively. MHC molecule is a cell surface molecule which is highly polymorphic. They can present the epitope peptides to the immune cells, induce proliferation of the corresponding immune cell population, and exert specific anti-tumor effects. According to a classic theory, the molecules binding to MHC I molecules are mainly endogenous antigenic peptides, which are generally 8-12 amino acids in length. The MHC-peptide complex is transferred to the cell surface, where the complex is recognized by the receptor of CD8 T cells. The molecules binding to MHC II molecules mostly are exogenous antigenic peptides, which vary greatly in length, generally 9-25 amino acids in length. This MHC-peptide complex is transferred to the cell surface, where the complex is recognized by the receptor of CD4 T cells. CD4 T cell is also called as Th cell, which can be divided into two types, namely Th1 type and Th2 type, based on the cytokines secreted. Th1 mainly secrets IL-2, IFN-γ and TNF-β, while Th2 mainly secrets IL-4, IL-5, IL-6 and IL-13. CD8 T cell is the classic CTL cell. Depending on the characteristics of immune responses by the organism against pathogens or tumors, specific Th and/or CTL epitopes may be selected to directionally induce Th and/or CTL response in the host. It is even possible to induce directional development of Th1 or Th2 immune response in the organism by selecting a Th1 epitope or Th2 epitope, thereby resulting in an effective induction and accurate regulation of immune response. Recent studies show that these two pathways are not completely independent from each other. The peptides obtained from treatment of exogenous antigens in the organism can also enter into MHC I molecule pathway and can be recognized by the receptor of CD8 T cells. It is a strong support in theory to the anti-tumor practice by using exogenous antigens. CD4 T cells mostly exert non-specific anti-tumor effects only, and the tumor-killing effects are indirect; whereas specific CD8 T cells may kill tumor cells more effectively and more directly. If exogenous antigens can enter into MHC I molecule pathway, they might induce specific CD8 T cells, thereby resulting in effective anti-tumor effects. In the meantime, it shows that the cell induction pathways for Th and CTL cells are closely associated. Functionally speaking, only when Th epitopes are present, can CTL epitopes induce immune responses or can induce immune responses more effectively. It is clear now that dendritic cells (DCs) and heat shock proteins are important for the above cross presentation. Therefore, identification of effective anti-tumor epitope peptides may provide a more accurate and effective means for mediating the anti-tumor immune response.

Currently, the methods for identifying epitope peptides mainly include enzymolysis; elution; synthesis of overlapping peptides; screening mimic epitopes by phage-display peptide library; predicting candidate epitope peptides by a computer, followed by experimental verification. Though the methodology for identifying epitope peptides is improving continuously, the operation thereof is still time-costing. In addition, the peptides obtained after screening might not be effective because of variation of tumors and the immune tolerance of the organisms against the tumors.

The epitope peptides of some malignant tumors such as colon carcinoma, melanoma, lymphoma, neuroglioma and prostate carcinoma have been prepared in some foreign countries, and some of them have entered into the clinical research stage and a preliminary efficacy has been established. There are few reports about the preparation and application of epitope peptides of ovarian cancer throughout the world.

SUMMARY OF THE INVENTION

In the present invention, BALB/c mice are immunized by a soluble antigen of epithelial ovarian carcinoma, OC166-9, to obtain an anti-ovarian cancer monoclonal antibody, COC166-9. Then BALB/c mice are immunized by COC 166-9 to obtain an Ab2β-type anti-idiotype antibody 6B11, which mimics the ovarian cancer antigen OC166-9, by hybridoma technique (for the details, see Chinese Application No. CN01130756.0 filed by the present applicant previously, which has been published under Publication No. CN 1356341 and has been granted). Two T-cell epitope peptides mimicking the ovarian cancer antigen are identified from the above-mentioned anti-idiotype antibody. These peptides are different from the original tumor antigens. They can help to disrupt the immune tolerance in the organism with tumors, and thus can be used in the regulation of the cell immune response against ovarian cancer and in monitoring clinical efficacy.

The inventors further identified the active components of ovarian cancer anti-idiotype antibody 6B11 which are effective for inducing a specific cellular immune response against ovarian cancer and obtained two T-cell epitope peptides. They are CDR3 region peptides in the heavy chain and the light chain of the anti-idiotype antibody respectively, with sequences of IALITTKIAWYFDV (SEQ ID NO:3) and SQSTHFPYT (SEQ ID NO:6) respectively.

These two T-cell epitope peptides can induce a stronger cellular immune response against ovarian cancer than the anti-idiotype antibody from which the peptides are derived. Therefore, these two peptides can be used to construct vaccines against ovarian cancer, to supplement the treatment of ovarian cancer, and to monitor the clinical efficacy and treatment effects of ovarian cancer vaccines.

The present invention also provides a process for preparing said T-cell epitope peptides of the anti-idiotype antibody.

The advantages of the present invention include:
1. The present T-cell epitope peptides of the anti-idiotype antibody are the active components of said anti-idiotype effective for inducing cellular immune response. The property of inducing specific cellular immune response against ovarian cancer of said anti-idiotype is remained, while the negative effects of inhibitory epitopes of the antibodies during the induction of immune response can be avoided.
2. The present T-cell epitope peptides of the anti-idiotype antibody contain Th and CTL epitopes. They can induce the response of CD4 and CD8 T cells simultaneously. Both the primary and secondary immune responses are good, and the anti-ovarian cancer immune response induced thereby is effective.
3. In the present T-cell epitope peptides of the anti-idiotype antibody, Th and CTL epitope peptides are relevant T-cell epitopes against the same tumor antigen, which are associated to each other. Their anti-ovarian cancer effect is more specific and effective than that of the unassociated combination of CTL epitope peptide and Th epitope peptide derived from bovine serum albumin, keyhole limpet hemocyanin and tetanus toxoid etceteras.
4. The present T-cell epitope peptides of the anti-idiotype antibody are derived from the anti-idiotype antibody 6B11, which are mimic peptides and different from the actual tumor antigens. They can disrupt the immune tolerance inherent in the organisms with tumors, thus exerting anti-tumor effects.

In one aspect, these two T-cell epitope peptides of the anti-idiotype antibody of the present invention can specifically kill OC166-9-positive ovarian cancer cells and can be used as a vaccine against ovarian cancer for treating ovarian cancer. They can also be combined with other T-cell epitope peptides against ovarian cancer and used as a vaccine against ovarian cancer for treating multiple types of ovarian cancers. In another aspect, these two T-cell epitope peptides of the anti-idiotype antibody of the present invention may be used to construct a fusion protein with a heat shock protein molecule, exerting the effect of a molecular chaperone, the effect of an immune adjuvant and the antigen cross presenting effect of the heat shock protein, for treating ovarian cancer as a vaccine against ovarian. These two T-cell epitope peptides of the anti-idiotype antibody can be co-synthesized with the binding sequence of the heat shock protein molecule respectively, and then reversibly bind to the heat shock protein molecule under appropriate ion conditions, and used to treat ovarian cancer as a vaccine against ovarian cancer by means of stimulating immune cells by the endogenous antigen peptide molecules. After the prepared vaccine is loaded by dendritic cells, autologous lymphocytes are stimulated. Several groups including a group stimulated only by T-cell epitope peptides, a group of non-dendritic cell loading (e.g., ray-radiated autologous peripheral blood monocytes) and the like are set to study the roles and cooperation of the heat shock protein molecule and DCs in the cross presentation of antigens. The peptides can be combined with different heat shock protein molecules (human or murine HSP70 and gp96) to prepare anti-ovarian cancer vaccines. The difference between the effects obtained when using homogenous and heterogenous molecules and the difference between the effects obtained when using HSP 70 and gp96 are observed, for purposes of providing theoretical evidence for selecting a heat shock protein molecule as a vaccine adjuvant and for providing references for studying the functional differences of heat shock protein molecules. In another aspect, as stimulating molecules in ELISPOT assay, these two T-cell epitope peptides of the anti-idiotype antibody of the present invention may be used to detect the number of specific cells produced after applying the anti-idiotype antibody or T-cell epitope peptides of the anti-idiotype antibody, thus monitoring the therapeutic responses and evaluating the efficacy of the treatment. Additionally, these two T-cell epitope peptides of the anti-idiotype antibody of the present invention can be used to prepare Tetramer I and II assay kits respectively using Th epitope peptide and CTL epitope peptide. The kits can be used to accurately quantify the number of CLT cells produced after applying anti-idiotype antibody 6B11 or T-cell epitope peptides of the anti-idiotype antibody, thus monitoring the effectiveness for inducing immune response.

DESCRIPTION OF THE DRAWINGS

FIG. 1 shows the expression profile of the surface molecules of mature dendritic cells.

FIG. 2 shows BrdU cell proliferation assay.

FIG. 3 shows the determination of the optimal application concentration of MHC class II molecule antibodies.

FIG. 4 shows BrdU cell proliferation assay after applying MHC class II molecule blocking antibodies.

FIG. 5 shows BrdU cell proliferation assay after sorting CD4 T cells.

FIG. 6 shows determination of the intracellular cytokines of CD4 T cells by flow cytometry.

FIG. 7 shows detection of the expression profile of MHC-I molecules on the surface of T2 cells (co-incubated with 30 μg/ml peptides) by confocal microscopy.

FIG. 8 shows detection of cytotoxic effect of peptide-specific CTLs by $^{51}$Cr release assay, wherein the peptide-specific CTLs are A) VH CDR1 peptide-specific CTLs; B) VH CDR2 peptide-specific CTLs; C) VH CDR3 peptide-specific CTLs; D) VL CDR1 peptide-specific CTLs; E) VL CDR2 peptide-specific CTLs; F) VL CDR3 peptide-specific CTLs; G) VH CDR2 predicted peptide-specific CTLs; H) VH CDR3 predicted peptide 1-specific CTLs; I) VH CDR3 predicted peptide 2-specific CTLs; and J) VL CDR3 predicted peptide-specific CTLs, respectively.

FIG. 9 shows determination of the optimal application concentration of MHC class I molecule antibodies.

FIG. 10 shows $^{51}$Cr release assay on the A) VH CDR3 (complementary determining region 3 of the heavy chain) peptide specific CTLs and B) VL CDR3 (complementary determining region 3 of the light chain) peptide specific CTLs after MHC class I molecule antibody blocking.

FIG. 11 shows detection of killing effects of the VH CDR3 and VL CDR3 peptide specific CTLs on K562 cells by $^{51}$Cr release assay.

FIG. 12 shows detection of effectiveness of killing ovarian cancer cells by the VH CDR3 and VL CDR3 peptide specific CTLs through $^{51}$Cr release assay.

FIG. 13 shows the expression profiles of cytokines of CTLs induced by VH CDR3 and VL CDR3 peptides as well as anti-idiotype antibody 6B11.

FIG. 14 shows the profiles of antigen-specific IFN-γ-producing cells among anti-idiotype antibody 6B11-CTLs as well as VH CDR3 and VL CDR3 region peptides specific CTLs.

DESCRIPTION OF DETAILED EMBODIMENTS

In one aspect, the present invention provides a T-cell epitope peptide, the amino acid sequence of which is shown in SEQ ID NO:3 or 6; or has a substitution, deletion or addition of one or several amino acids compared with the amino acid sequence shown in SEQ ID NO:3 or 6, and has substantially the same biological activity as that of SEQ ID NO: 3 or 6. The term of "having substantially the same biological activity" means that the variant has an observable biological activity of the T-cell epitope peptide as shown in SEQ ID NO: 3 or 6, including inducing cellular immune response against ovarian cancer, triggering the proliferation of T cells and the like.

In another aspect, the present invention provides nucleic acid molecules encoding said T-cell epitope peptides and vectors comprising said nucleic acid molecules.

In a further aspect, the present invention provides a pharmaceutical composition for the treatment or prevention of ovarian cancer, comprising the epitope peptide of the present invention as an active ingredient and a pharmaceutically acceptable carrier. There is no special limit to the carrier, which may be conventional carriers known in the art, including, for example, lactose, sodium carbonate, corn starch, alginic acid, water, mineral oil and etc.

In a still further aspect, the present invention provides a vaccine against ovarian cancer, wherein said vaccine comprises the epitope peptide of the present invention and a heat shock protein.

The present invention also provides a method for the treatment or prevention of ovarian cancer, comprising administering to a subject a therapeutically or prophylactically effective amount of the epitope peptide or the pharmaceutical composition of the present invention. The "therapeutically or prophylactically effective amount" can be determined by the skilled in the art based on particular settings.

Particularly preferably, the epitope peptide of SEQ ID NO: 3 and the epitope peptide of SEQ ID NO: 6 can be administered simultaneously, sequentially or separately for a better efficacy.

The present invention also provides the use of said epitope peptides in the manufacture of a medicament and a kit.

The following examples are provided in combination with appended drawings for illustrating the present invention in more details. These examples are provided for the purpose of illustration only and should not be construed to limit the scope of the present invention in any way.

Example 1

Preparation of Ovarian Cancer Anti-Idiotype Antibody 6B11

For the detailed preparation procedure, see earlier application CN01130756.0 (Publication No. CN1356341) filed by the applicant. The technical route comprises two major steps as below:
1. Immunizing BALB/c mice by a soluble antigen of epithelial ovarian carcinoma, OC166-9, to obtain an anti-ovarian cancer monoclonal antibody, COC166-9, by hybridoma technique.
2. Immunizing BALB/c mice by COC 166-9 to obtain an anti-idiotype antibody by hybridoma technique, wherein said anti-idiotype antibody mimics the ovarian cancer antigen OC166-9.

Example 2

Identification of T-cell Epitope Peptides of Said Anti-Idiotype Antibody 6B11 and Determination of the Ability of Inducing Immune Response The technical route is set forth below:
I. Preparation of Peripheral Blood Monocyte Derived DCs and Loading With Anti-Idiotype Antibody 6B11 and the Peptides
(I) Isolation of Peripheral Blood Monocytes Peripheral blood was drawn from HLA-A2 healthy human subjects. After EDTA anti-coagulation treatment, peripheral blood monocytes were isolated using Ficoll lymphocyte isolation $1 \times 10^7$ monocytes/well and AIM-V culture medium (containing 5% human AB serum) was added to 1 ml. The cells were incubated at 37° C. under 5% $CO_2$ for 2 hours. Non-adherent cells were drawn and removed as lymphocytes and stored in liquid nitrogen for further use. The adherent cells were monocytes.
(II) Induction Incubation of DCs (Dendritic Cells) and Analysis on Mature Phenotypes The monocytes isolated from said 6-well plates were added with 2 ml AIM-V culture medium (containing 5% human AB serum)/well. Recombinant human granulocyte-macrophage colony-stimulating factor (rh GM-CSF) and recombinant human interleukin-4 (rh IL-4) were added simultaneously both to a final concentration of 1000 U/ml, for induced incubation. On Day 4, 1 ml AIM-V culture medium (containing 5% human AB serum) was supplemented, and rh GM-CSF and rh IL-4 of the same concentration as mentioned above were also supplemented. On Day 6, 1 ml AIM-V culture medium (containing 5% human AB serum) was supplemented again. At the same time, recombinant human tumor necrosis factor-α (rh TNF-α), recombinant human α-interferon (rh IFN-α) and recombinant human interleukin-6 (rh IL-6) were added, all to a final concentration of 1000 U/ml, and prostaglandin E2 (PGE2) was added to a final concentration of 1 μg/ml. Co-incubation lasted 24 hours for inducing mature DCs.

DCs were harvested, washed and adjusted to a concentration of 1×10$^6$ cells per 10 ml centrifuge tube. 5 μl/tube of FITC- and PE-labeled fluorescent antibodies were added. Labelling was carried out in dark at 4° C. for 30 min. Washing step was performed twice. The expression profiles of CD80, CD86, CD83, CD1a and HLA-DR molecules on the surface of the mature DCs induced were analyzed by flow cytometry (FIG. 1).

(III) Loading DCs With Anti-Idiotype Antibody 6B11 and CDRs (Complementary Determining Region) Region Peptides of Anti-Idiotype Antibody 6B11

(1) Loading DCs With Anti-Idiotype Antibody 6B11

On Day 4 during incubation of DCs, the culture medium, rh GM-CSF and rh IL-4 were supplemented. At the same time, anti-idiotype antibody 6B11 was added to a final concentration of 40 μg/ml for loading. The loaded cells were stored as stimulating cells for further use.

(2) Loading DCs With CDR Peptides of Anti-Idiotype Antibody 6B11

Mature DCs induced were harvested, washed and adjusted to a concentration of 1×10$^6$ cells/ml. Six CDR peptides (SEQ ID NOs: 1-6, see Table 1, artificially synthesized) in a final concentration of 30 μg/ml respectively, or each peptide of 30 μg/ml together with keyhole limpet hemocyanin (KLH) of 5 μg/ml were added for loading. The loaded cells were stored as stimulating cells for further use.

II. Inducing Specific CTLs by Anti-Idiotype Antibody 6B11 and CDR Peptides of Anti-Idiotype Antibody 6B11

(I) Inducing CTLs Specific to Anti-Idiotype Antibody 6B11

The freeze-stored autologous lymphocytes were stimulated by DCs loaded with anti-idiotype antibody 6B11 (anti-Id DCs), to obtain CTLs specific to anti-idiotype antibody 6B11 (6B11-CTLs). One period consists of 7 days. On Day 3 of every period, 10 U/ml recombinant human interleukin-2 (rh IL-2) was supplemented. Finally, anti-idiotype antibody 6B11-CTLs were obtained after a one- or three-period stimulation.

(II) Inducing CTLs Specific to CDR Peptides of Anti-Idiotype Antibody 6B11

The freeze-stored autologous lymphocytes were stimulated by DCs loaded with the peptides and KLH, to obtain peptide-specific CTLs (peptide-CTLs). One period consists of 7 days. On Day 3 of every period, 10 U/ml rh IL-2 was supplemented. Finally, peptide-CTLs were obtained after a 3-period stimulation.

6B11-CTLs stimulated for one period were harvested and used as reacting cells in cell proliferation assay, ELISA cytokine assay and IFN-γ ELISPOT assay. 6B11-CTLs and peptide-CTLs stimulated for 3 periods were harvested for use in $^{51}$Cr release assay as effector cells.

III. Identification of Th Epitope Peptides of Anti-Idiotype Antibody 6B11 and Analysis of the Types of the Immune Responses Induced Thereby (I) Identification of Th Epitope Peptides of Anti-Idiotype Antibody 6B11 by BrdU ELISA Cell Proliferation Assay All the CDR peptides of anti-idiotype antibody 6B11 (6 peptides) were synthesized artificially. The peptides were screened for Th epitope peptides by cell proliferation assay. Anti-idiotype antibody 6B11-CTLs stimulated for one period were used as reacting cells. DCs loaded with anti-idiotype antibodies and peptides respectively were used as stimulating cells. The reacting cells and the stimulating cells (in the ratio of 10:1) were co-incubated at 37° C. under 5% $CO_2$ for 120 hours and then subject to BrdU ELISA cell proliferation assay. Each well contained 100 μl AIM-V culture medium and 1×10$^5$ anti-idiotype antibody 6B11-CTLs. Within the last 2 hours during stimulation, 10 μl BrdU labeling solution was added into each well and the fluid in the wells was removed. The cells were dried at 60° C. for 1 hour. 200 μl of FixDenat solution was added into each well. The reaction continued for 30 minutes at 37° C. for fixing DNA in the lymphocytes. Finally, 100 μl BrdU monoclonal antibody was added into each well for 90 minutes. The absorption value at 450 nm was read by an automatic microplate reader after substrate chromogenic reaction for detecting the proliferation of the cells. The group of DCs without loading and the group of phytohaemagglutinin (PHA) were used as negative and positive control respectively. The results showed significant proliferation of the reacting cells 6B11-CTLs upon stimulation by positive control (PHA). That meant the reacting cells used in this experiment had a good ability of proliferation, which could proliferate normally when subject to peptides specific to T-cell receptors. 6B11-DCs could stimulate proliferation of the reacting cells because they had all the peptide fragments of a full-length anti-idiotype antibody. Among the 6 CDR peptides, only heavy chain (VH) CDR3 peptide (SEQ ID NO:3) and light chain (VL) CDR3 peptide (SEQ ID NO:6) could stimulate the proliferation of the reacting cells, wherein the effect of the former was stronger. Other peptides could not stimulate the proliferation of the reacting cells. That indicated that VH CDR3 and VL CDR3 peptides were key portions of the anti-idiotype antibody for exerting its effects (FIG. 2).

For further analyzing the proliferation of the cells, stimulating cells were blocked by anti-human MHC class II antibodies, for evaluating the effect of Th epitope peptides. Firstly, the optimal application concentration of MHC class II antibodies was determined by experiments to be 1:20 dilution (FIG. 3). The results of cell proliferation assay after blocking by MHC class II antibodies showed that the proliferation triggered by PHA and 6B11-DCs were blocked dramatically by MHC class II antibodies. The proliferation triggered by VH CDR3 peptide could be blocked mostly by MHC class II antibodies; while the proliferation triggered by VL CDR3 peptide could not be blocked by MHC class II antibodies. Other peptides could not trigger cell proliferation, no matter whether MHC class II antibodies were applied or not (FIG. 4). The results indicated that similar to PHA, VH CDR3 peptide mainly trigger the proliferation of CD4 T cells, while the proliferation triggered by VL CDR3 peptide was irrelevant to CD4 T cells. The reacting cells were subject to magnetic bead sorting of CD4 T cells. Thereafter, the results of the cell proliferation assay conducted thereon showed that in addition to PHA and 6B11-DCs, only VH CDR3 peptide could trigger the proliferation of CD4 T cells, whereas VL CDR3 peptide could not trigger the proliferation of CD4 T cells, which was consistent with the above experimental results (FIG. 5). It indicated that VH CDR3 peptide (IALITTKIAWYFDV, SEQ ID NO:3) could indeed induce the proliferation of CD4 T cells in 6B11-CTLs, which was a Th epitope peptide of the anti-idiotype antibody 6B11.

(II) Determination of the Types of the Immune Responses Induced by Th Epitope Peptides by Assaying Intracellular Cytokines Through Flow Cytometry.

The anti-idiotype antibody 6B11-CTLs were co-incubated respectively with DCs loading VH CDR3 peptides and DCs without loading. The production of intracellular cytokines in CD4 T cells derived from the anti-idiotype antibody 6B11-CTLs was detected by flow cytometry. The results showed that VH CDR3 peptide could stimulate a high level of IFN-γ secretion by CD4 T cells and a low level of IL-4 (FIG. 6). The results indicated that VM CDR3 peptide (IALITTKIAWY-FDV, SEQ ID NO:3), as a Th epitope peptide of the anti-idiotype antibody, mainly induce Th1-type immune response.

IV. Identification of CTL Epitope Peptides of the Anti-Idiotype Antibody 6B11.

(I) Prediction of HLA-A2 Binding Peptides from CDR Peptides of the Anti-Idiotype Antibody 6B11 by SYFPEITHI Method.

The sequences of the CDR peptides of the anti-idiotype antibody 6B11 were input into a prediction website (http://www.uni-tuebingen.de/uni/kxi/), analyzing for potential HLA-A2 binding peptides among these sequences and obtaining the prediction scores. 13 binding peptides with a score of >7 were selected: 4 were located in VH CDR2 region, 4 in VH CDR3 region, 4 in VL CDR1 region and 1 in VL CDR3 region. Only 9-mer or 10-mer HLA-A2 binding peptides could be predicted by this method. In order to avoid missing any potential sequences, we synthesized artificially the above thirteen 9-mer peptides with a score of >7 and two 8-mer peptides of VH CDR 1 and VL CDR2 regions for further experiments (Table 1).

(II) Screening HLA-A2 Binding Peptides from CDR Peptides of the Anti-Idiotype Antibody 6B11 by T2 Cell Binding Assay.

The peptides obtained by SYFPEITHI method and the VH CDR1 and VL CDR2 region peptides were subject to T2 cell binding assay. T2 cells were co-incubated with each peptides in different concentrations (0.3 µg/ml, 3 µg/ml and 30 µg/ml) for 24 hours and then co-incubated with anti-human MHC class I antibodies. The expression profile of HLA class I molecules on the surface of T2 cells was analyzed by confocal microscopy. The results showed that the VH CDR2 region peptide (NNKYYNTAL, SEQ ID NO: 10) had high binding capacity; the VL CDR3 region peptide (SQSTHFPYT, SEQ ID NO:6) had moderate binding capacity, while the VH CDR 3 region peptides (LITTKIAW (SEQ ID NO:11) and IALITTKIA (SEQ ID NO:13)) and VL CDR1 region peptide (VHSNGNTYL, SEQ ID NO:16) had low binding capacity (Table 1 and FIG. 7). NNKYYNTAL (SEQ ID NO:10), LITTKIAW (SEQ ID NO:11), IALITTKIA (SEQ ID NO:13) and VHSNGNTYL (SEQ ID NO:16) were new peptides screened. They were synthesized together with the CDR peptides of the anti-idiotype antibody for screening CTL epitope peptides.

TABLE 1

Screening HLA-A2 binding peptides from CDR peptides of anti-idiotype antibody 6B11

| CDRs | Sequences of CDRs | Predicted peptides | SYFPEITHI score | T2 binding |
|---|---|---|---|---|
| VH CDR1 | PTYGIGVG (SEQ ID NO: 1) | PTYGIGVG (SEQ ID NO: 1) | 0 | − |
| VH CDR2 | HIWWNNNKYYNTA LKS (SEQ ID NO: 2) | HIWWNNNKY (SEQ ID NO: 7) | 12 | − |
|  |  | NNKYYNTAL (SEQ ID NO: 8) | 10 | +++ |
|  |  | NNNKYYNTA (SEQ ID NO: 9) | 9 | − |
|  |  | WNNNKYYNT (SEQ ID NO: 10) | 7 | − |
| VH CDR3 | IALITTKIAWYFDV (SEQ ID NO: 3) | LITTKIAWY (SEQ ID NO: 11) | 16 | + |
|  |  | ALITTKIAW (SEQ ID NO: 12) | 15 | − |
|  |  | IALITTKIA (SEQ ID NO: 13) | 13 | + |
|  |  | TKIAWYFDV (SEQ ID NO: 14) | 12 | − |
| VL CDR1 | RSSQNLVHSNGNTY LH (SEQ ID NO: 4) | NLVHSNGNT (SEQ ID NO: 15) | 14 | − |
|  |  | VHSNGNTYL (SEQ ID NO: 16) | 13 | + |
|  |  | SSQNLVHSN (SEQ ID NO: 17) | 10 | − |
|  |  | LVHSNGNTY (SEQ ID NO: 18) | 9 | − |
| VL CDR2 | PIVSNRIFS (SEQ ID NO: 5) | PIVSNRFS (SEQ ID NO: 5) | 0 | − |
| VL CDR3 | SQSTHFPYT (SEQ ID NO: 6) | SQSTHFPYT (SEQ ID NO: 6) | 7 | ++ |

(III) Identification of CTL Epitope Peptides of the Anti-Idiotype Antibody 6B11 by $^{51}$Cr Release Assay 6B11-CTLs and peptide-CTLs stimulated for three periods were used as effector cells. T2 cells, HOC1A cells and HLE cells loaded with corresponding peptides were used as target cells. Standard $^{51}$Cr release assay was carried out for 4 hours. Target cells (1×10$^6$ cells) were placed into 0.5 ml RPMI 1640 culture medium (containing 5% fetal bovine serum). 100 µCi Na$_2$$^{51}$CrO$_4$ was added. The labeling reaction was allowed to continue overnight at 37° C. Then the cells were washed by cold RPMI 1640 culture medium (containing 5% fetal bovine serum) for three times to terminate the labeling reaction. Target cells (5×10³ cells) were placed into 100 μl culture medium and then mixed with an equal volume of effector cells in a 96-well plate. The ratio of effector/target was set as 40:1, 20:1, 10:1 and 5:1. Spontaneous release wells contained target cells and the culture medium, while the maximal release wells contained target cells and corresponding culture medium containing 1% Triton X-100. The plates were gently spun using a plate centrifuge for 2 minutes and then co-incubated at 37° C. under 5% $CO_2$ for 4 hours. The plates were gently spun again. 100 μl of supernatant per well was transferred to a counting tube and labeled as appropriate. The cpm values were determined by a γ counter. All assays were performed in duplicate. The ratio of cpm values of the spontaneous release well to the maximal release well was <20%.

Killing ratio (%)=[(mean cpm value of the experimental wells−mean cpm value of the spontaneous release wells)/(mean cpm value of the maximal release wells−mean cpm value of the spontaneous release wells)]×100

The results showed that VH CDR3 peptide-CTLs could kill HOC1A cells and T2 cells loaded with said peptide. This indicated that VH CDR3 indeed was an epitope peptide responsible for the killing effect in the anti-idiotype antibody. In addition, this epitope peptide was also a predominant epitope peptide of the ovarian cancer antigen, OC166-9 and could participate in the induction of immune response (FIG. 8-C). VL CDR3 peptide-CTLs could also kill HOC1A cells and T2 cells loaded with said peptide. It was also a predominant epitope peptide responsible for the killing effect in the anti-idiotype antibody (FIG. 8-F). With lowering of the effector/target ratio, the killing ratios of 6B11-CTLs, VH CDR3 peptide-CTLs and VL CDR3 peptide-CTLs against target cells were lowered. Other peptide-CTLs could not kill HOC1A cells and T2 cells stimulated with corresponding peptides. They were peptides unrelated to T-cell killing effect in anti-idiotype antibody 6B11 (FIGS. 8A, B, D, E, G-J).

For further analyzing the above-mentioned killing effect, the target cells were blocked by applying anti-human MHC class I antibodies, for evaluating the effect of CTL epitope peptides. Firstly, the optimal concentration of MHC class I antibodies was determined to be 1:20 dilution (FIG. 9). The experimental results of $^{51}$Cr release assay carried out after blocking MHC class I molecules showed that VH CDR3 peptide-CTLs could still kill T2 cells and HOC1A cells stimulated with the peptide upon MHC class I molecule blocking. The killing effect were not disturbed by MHC class I antibodies, i.e., unrelated to the effect of CD8 T cells. The killing effect of VL CDR3 peptide-CTLs on T2 cells and HOC1A cells stimulated with the peptide upon MHC class I molecule blocking was significantly inhibited. Its killing effect was disturbed by MHC class I antibodies, which was mainly mediated by CD8 T cells (FIG. 10). This indicated that the underlying mechanism for VH CDR3 peptides and VL CDR3 peptides were different, though both of them could trigger a killing effect. The former was unrelated to CD8 T cells whereas the latter was mediated by CD8 T cells. This also indicated that VL CDR3 peptide (SQSTHFPYT) was a CTL epitope peptide of anti-idiotype antibody 6B11.

V. Determination of the Biological Activity of T-Cell Epitope Peptides of Anti-Idiotype Antibody 6B11

(I) Determination of Specificity and Effectiveness of the Killing Effect of T-cell Epitope Peptides of Anti-Idiotype Antibody 6B11 by $^{51}$Cr Release Assay The specific CTL cells induced by Th epitope peptide (namely VH CDR3 peptide), CTL epitope peptide (namely VL CDR3 peptide) and anti-idiotype antibody 6B11 were used as effector cells, and K562 cells and HOC1A cells were used as target cells for performing $^{51}$Cr release assay, in order to detect the specificity of the killing effect of Th epitope peptide and CTL epitope peptide and compare with that of anti-idiotype antibody 6B11. T cells stimulated by non-loaded DCs and naive T cells were used as negative controls. The results showed that VH CDR3 peptide-CTLs could kill K562 cells and a non-specific effecting mechanism existed; whereas VL CDR3 peptide-CTLs could not kill K562 cells and no non-specific effecting mechanism existed (FIG. 11). Both VH CDR3 peptide and VL CDR3 peptide were effecting parts of the anti-idiotype antibody 6B11 and both of them were involved respectively in the non-specific and specific effecting mechanisms induced.

For investigating the specificity and effectiveness of the killing effect of T-cell epitope peptides, the following experiments were carried out. T cells were stimulated by VH CDR3 peptide (30 μg/ml, final concentration), VL CDR 3 peptide (30 μg/ml), VH CDR3 peptide (15 μg/ml) and VL CDR3 peptide (15 μg/ml) as well as anti-idiotype antibody 6B11 (40 μg/ml), resulting in corresponding specific CTLs, which were used as effector cells. HOC1A cells were used as target cells for performing $^{51}$Cr release assay, in order to compare the effectiveness of each antigen in stimulating immune responses. The results showed that both VH CDR3 peptide-CTLs and VL CDR3 peptide-CTLs could kill target cells HOC1A. The killing effect of the specific CTLs obtained by stimulating with the combination of VH CDR3 peptide and VL CDR3 peptide was even stronger, which indicated a synergic effect between them. The killing effect of them was also stronger than that of 6B11-CTLs (FIG. 12). This further proved that VH CDR3 peptide and VL CDR3 peptide were the active components responsible for inducing T-cell response in the anti-idiotype antibody 6B11. Their effects were more accurate than that of anti-idiotype antibody 6B11.

(II) Determination of the Profile of Cytokines Induced by T-Cell Epitope Peptides by ELISA 6B11-CTLs, VH CDR3-CTLs and VL CDR3-CTLs were mixed with target HOC1A cells in the ratio of 40:1 respectively and co-incubated at 37° C. under 5% $CO_2$ for 48 hours. The supernatant was harvested, and the contents of IL-2, IFN-γ and IL-4 determined by double-antibody-sandwich ELISA. The results showed that 6B11-CTLs could secrete high levels of IL-2 and IFN-γ while the secretion of IL-4 was in a low level. This indicated that there existed a Th1 or Tc1 polarization phenomenon in the immune response induced by anti-idiotype antibody 6B11. VH CDR3 peptide-CTLs could also secrete high levels of IL-2 and IFN-γ while the secretion of IL-4 was in a low level, which indicated that Th1 type immune response was induced. VH CDR3 peptide- and VL CDR3 peptide-specific CTLs could also secrete high levels of IL-2 and IFN-γ while the secretion of IL-4 was in a low level, which was in a similar trend as that of the immune response induced by anti-idiotype antibody 6B11. This indicated from a different perspective that VH CDR3 peptide and VL CDR3 peptide were involved in the induction of T cell immune response derived from anti-idiotype antibody 6B11 (FIG. 13).

(III) Determination of the Frequency of Specific Cells Secreting IFN-γ by Elispot Method Elispot method could be used to accurately detect the production of antigen-specific cytokines in the level of s single cell and count for the number of antigen-specific cells. It was one of the most effective methods for monitoring immune responses. 6B11-CTLs, VH CDR3 peptide- and VL CDR3 peptide-specific CTLs (as the reacting cells) were co-incubated with HOC1A and HLE cells (as the stimulating cells) for 24 hours. Then they were subject to the determination of the number of antigen-specific IFN-γ-secreting cells. The results showed that all of 6B11-CTLs, VH CDR3 peptide- and VL CDR3 peptide-specific CTLs could respond to HOC1A cells and the frequency of IFN-γ-secreting cells were $196/1\times10^6$ T cells and $184/1\times10^6$ T cells. Both were statistically significantly different from the group of T cells stimulated by non-loaded DCs and the group of naive T cells. The responses to HLE cells of all the T-cell groups were comparable and the frequencies of IFN-γ-secreting cells were similar (FIG. 14). The results showed that both anti-idiotype antibody 6B11 and VH CDR3 and VL CDR3 peptides could induce antigen-specific T cell response and that IFN-γ was the effector molecule of such an antigen-specific T-cell.

VI. Use of T-Cell Epitope Peptides of Anti-Idiotype Antibody 6B11 in the Construction of Ovarian Cancer Vaccines The information on ovarian cancer antigens is very limited up to now and specific T cell epitope peptides are not available for constructing vaccines against ovarian cancer. The epitope peptides of the present invention are important for constructing vaccines against ovarian cancer. The following will exemplify the use of T-cell epitope peptides in the construction of a vaccine against ovarian cancer, using heat shock protein as an example.

(I) Construction of a T-Cell Epitope Peptide-Heat Shock Protein Vaccine Against Ovarian Cancer (1) Theoretical Basis T-cell epitope peptide is prone to be degraded when used alone. Currently heat shock protein is considered to be the most desirable carrier for constructing a peptide vaccine. Its advantages are as below: allogeneic reaction could be avoided because of its high homology between different genera/species; degradation of the peptide may be prevented after binding to the peptide or form a fusion protein with the peptide; the peptide could be directed into corresponding immune-stimulating pathways to improve the accuracy of the effect of the peptides; antigen-presenting cells may be activated for facilitating secretion of cytokines and thus enhancing immune response; and antigen cross presentation may be facilitated.

(2) Construction Strategy

1) Construction of a Fusion Protein of a T Cell Epitope Peptide and a Heat Shock Protein as a Vaccine Against Ovarian Cancer.

i) Construction, Expression and Identification of a Fusion Protein of a T Cell Epitope Peptide and a Heat Shock Protein.

A plasmid comprising a histone-tagged fusion gene of T-cell epitope peptide and a heat shock protein was constructed using gene cloning techniques, DNA recombination techniques and PCR techniques (plasmid of CTL peptide-heat shock protein, plasmid of Th peptide-heat shock protein, plasmid of CTL peptide-linker-Th peptide-heat shock protein, plasmid of CTL peptide-linker-general Th peptide-heat shock protein, plasmid of unrelated CTL peptide-heat shock protein and plasmid of general Th peptide-heat shock protein). *E. coli* EL21 (DE3) was used as expression strain. After IPTG induction, the fusion protein of T-cell epitope peptide-heat shock protein was expressed as an inclusion body. In order to recover the conformation and the solubility of the heat shock protein, the fusion protein of T-cell epitope peptide and heat shock protein was purified by Ni-binding column with his-tag and renatured. The biological activity of the heat shock protein in the fusion protein was determined by ELISA and Western blot. The ATPase activity of the heat shock protein was determined by monitoring the radiation amount of $^{32}P$ released from ATP, using $^{32}P$ labeled ATP as a substrate. SDS PAGE gel electrophoresis and sequencing were carried out for determining the molecular weight of the fusion protein and for verifying the sequence.

ii) Determination of Anti-ovarian-cancer Effect of the Fusion Protein Vaccine of T-cell Epitope Peptide and Heat Shock Protein in an in Vitro Experiment in Patients With Ovarian Cancer.

DCs were incubated and induced to mature. DCs loaded with a fusion protein of a T-cell epitope peptide and a heat shock protein, DCs loaded with a fusion protein of an unrelated T-cell epitope peptide and a heat shock protein and non-loaded DCs were used as negative controls. These groups of DCs were used to stimulate autologous T-cells of patients with ovarian cancer. The composition of the effector cells and the stimulation profile were analyzed by flow cytometry. The expression profile of the cytokines (IL-2, IL-4, INF-γ and TNFα, etc.) in the supernatant of the culture of effector cells was assayed by ELISA and the polarity of the effector cells (Th1/Tc1 polarization or Th2/Tc2 polarization) evaluated. The number of antigen-specific effector cells was determined by ELISPOT. The anti-ovarian-cancer effect of the effector cells was detected by $^{51}Cr$ release assay.

iii) Determination of Anti-Ovarian-cancer Effect of the Vaccine Comprising the Fusion Protein of T-cell Epitope Peptide and Heat Shock Protein by Animal Experiments.

SCID mouse ovarian cancer model was constructed. The fusion protein vaccine of T-cell epitope peptide and heat shock protein was injected subcutaneously into the mice. The general health, tumor growth and production of ascitic fluid as well as the average survival period were observed and recorded. Tumor tissues were removed from SCID mice, sliced and immunohistologically stained to determine the type, the number and the variation with time of the tumor infiltrating lymphocytes.

2) Construction of a Vaccine Against Ovarian Cancer Comprising a T-Cell Epitope Peptide Reversibly Binding to a Heat Shock Protein.

Heat shock proteins were expressed and identified. T-cell epitope peptides and heat shock protein binding sequences were synthesized. The concentration of the heat shock protein was determined by Bio-Rad method. The peptide and the heat shock protein were mixed in a binding buffer at a ratio of 10:1 and incubated at 37° C. for 1 hour. Free peptides were removed by Microcon 50 molecule exclusion. The reversible binding of the T-cell epitope peptide to the heat shock protein was detected by mass spectrometry, gel electrophoresis and ATPase activity analysis. The anti-ovarian-cancer effect of the constructed vaccine was detected by in vitro experiments in patients with ovarian cancer and animal experiments (for details, see related experiments in Construction Strategy).

(II) Construction of Multi-Epitope Peptide Vaccine Against Ovarian Cancer by Using T-Cell Epitope Peptides.

Tumor antigens have certain differences between individuals, and tumor antigens are prone to vary under the pressure of immune selection of the organism, even when the tumor antigens are the same. Therefore, the peptides derived from a certain antigen are not suitable for all the patients with tumors. Said T-cell epitope peptides of the anti-idiotype antibody are T-cell epitope peptides mimicking tumor antigens, and therefore they could overcome the immune tolerance of the peptides derived from tumor antigens; however, due to the limitation of MHC, there is still a need for constructing a vaccine against ovarian cancer by combining with other ovarian cancer related T-cell epitope peptides, so as to enlarge the application of the ovarian cancer vaccine. The carrier could also be a heat shock protein (see above for details of the construction) while said T-cell epitope peptides of anti-idiotype antibody were combined with other T-cell epitope peptides (e.g., derived from P53) for co-construction.

VII. Use of T-cell Epitope Peptides of Anti-Idiotype Antibody 6B11 in the Construction of an Assay Kit (I) Theoretical Basis MHC molecules, T-cell epitope peptides and β2 microglobulin are basic units recognized by T-cell receptors. A complex constructed from these three molecules may be used to detect the T cells having receptors of the corresponding T-cell epitope peptides, thereby reflecting the therapeutic reaction after administration of the ovarian cancer vaccine comprising the epitope peptides and evaluating the efficacy thereof.

(II) Construction Strategy

The genes encoding β2 microglobulin and MHC molecule were cloned into a prokaryotic vector and expressed in *E. coli* respectively. The two expression products and T-cell epitope peptides (in a molar ratio of 1:2:40) were dialyzed at 4° C. (by dialysis method), or co-diluted with the peptides in 200 ml buffer and incubated at 10° C. (by dilution method). The obtained complex was biotinylated by using BirA enzyme. The biotinylated complex was then mixed with phycoerythrin-labeled avidin in a ratio of 4:1. Thus a Tetramer assay kit was constructed.

The invention claimed is:

1. An isolated epitope peptide, wherein the amino acid sequence of the epitope peptide is SEQ ID NO: 3 or 6.

2. The isolated epitope peptide according to claim 1, wherein the amino acid sequence of the epitope peptide is SEQ ID NO:3.

3. The isolated epitope peptide according to claim 2, wherein the epitope peptide is a Th epitope peptide.

4. The isolated epitope peptide according to claim 1, wherein the amino acid sequence of the epitope peptide is SEQ ID NO:6.

5. The isolated epitope peptide according to claim 4, wherein the epitope peptide is a CTL epitope peptide.

6. The isolated epitope peptide according to claim 1, wherein the epitope peptide induces a cellular immune response against ovarian cancer.

7. An assay kit, comprising the epitope peptide according to claim 1.

8. A method for the treatment of ovarian cancer, comprising administering to a subject a therapeutically or prophylactically effective amount of the epitope peptide according to claim 1.

9. A method for the treatment of ovarian cancer, comprising administering the epitope peptide of SEQ ID NO: 3 and the epitope peptide of SEQ ID NO: 6 simultaneously, sequentially or separately.

* * * * *